United States Patent [19]

Dunklee

[11] Patent Number: 5,082,112
[45] Date of Patent: Jan. 21, 1992

[54] PACKAGE FOR ENDOSCOPIC LIGATING INSTRUMENT

[75] Inventor: Douglas M. Dunklee, Bridgeport, Conn.

[73] Assignee: United States Surgical Corporation, Norwalk, Conn.

[21] Appl. No.: 650,744

[22] Filed: Feb. 5, 1991

[51] Int. Cl.⁵ .............................................. B65D 75/26
[52] U.S. Cl. ................................... 206/363; 206/471
[58] Field of Search .............................. 206/363–365, 206/438, 461–471

[56] References Cited

U.S. PATENT DOCUMENTS

| | | | |
|---|---|---|---|
| 3,476,114 | 11/1969 | Shannon et al. | |
| 3,476,115 | 11/1969 | Graeff et al. | |
| 3,910,410 | 10/1975 | Shaw | 206/471 |
| 4,106,621 | 8/1978 | Sorenson | 206/470 |
| 4,324,331 | 4/1982 | Ignasiak | 206/461 |
| 4,676,446 | 6/1987 | Ciocarelli et al. | 206/470 |
| 4,730,726 | 3/1988 | Holzwarth | 206/471 |
| 5,031,775 | 7/1991 | Kane | 206/571 |

Primary Examiner—Jimmy G. Foster
Attorney, Agent, or Firm—Thomas R. Bremer; Peter G. Dilworth; Rocco S. Barrese

[57] ABSTRACT

A packaging unit for an endoscopic ligating loop instrument includes a molded instrument holding member and a cover member.

21 Claims, 3 Drawing Sheets

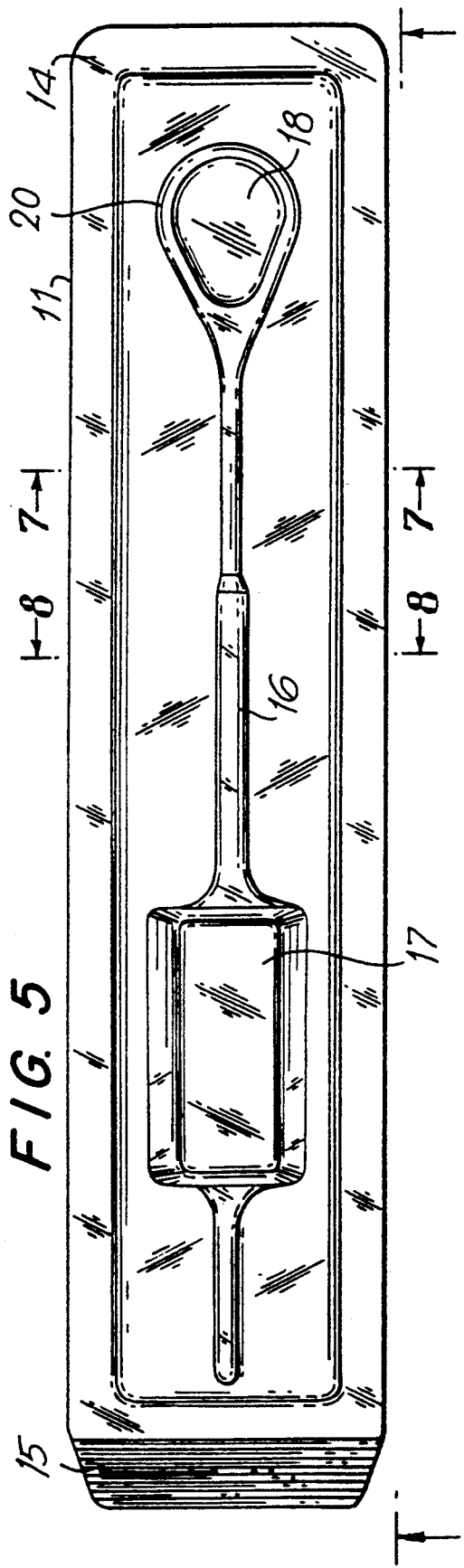
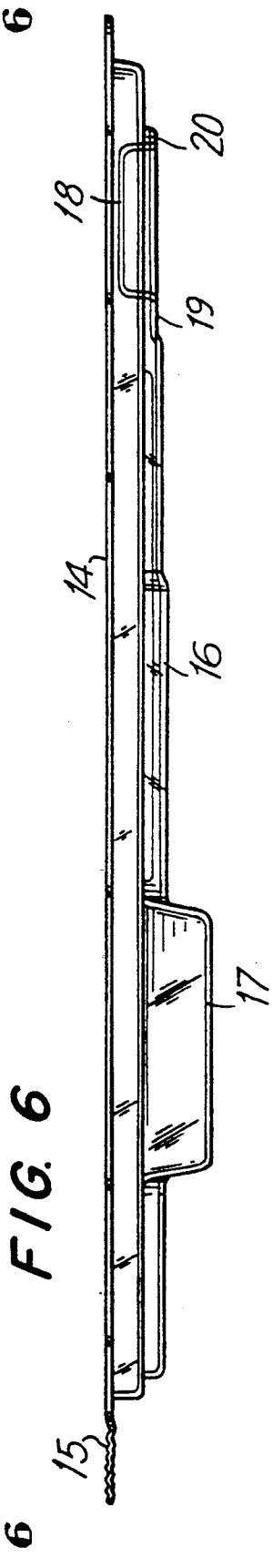
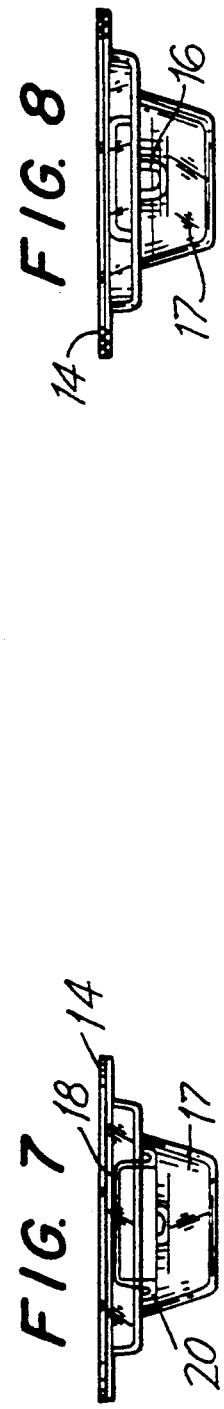
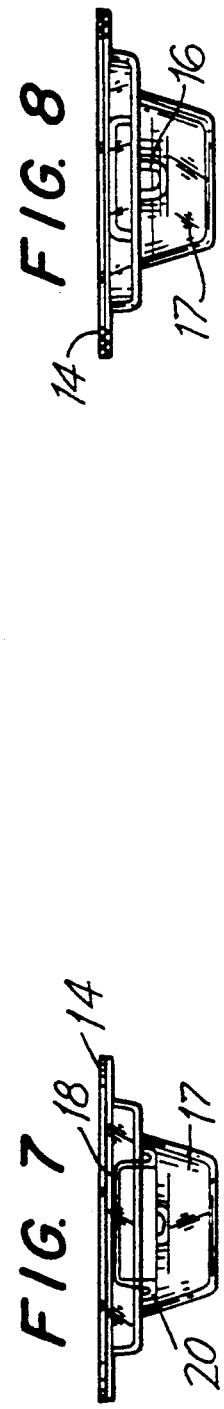

PACKAGE FOR ENDOSCOPIC LIGATING INSTRUMENT

BACKGROUND OF THE INVENTION

This invention relates to a package for an endoscopic ligating instrument possessing a loop, or "noose", ligating element.

In the ligating instrument described in U.S. Pat. Nos. 3,476,114 and 3,476,115, an elongated tubular body member carries a ligature within its shaft, the ligature terminating in an external loop which is intended to be drawn tightly about a severed vessel to achieve hemostasis. An instrument of this type is currently being marketed in a packaging unit which includes a relatively stiff retainer card upon which the instrument is mounted with one end of the instrument being held in place at one end of the retainer card by means of a die-cut securing strap positioned near this end of the card and the other, or loop, end of the instrument being held in place at the opposite end of the retainer card through the tensioned engagement of the loop upon a semicircular retainer card extension at such opposite end. The retainer card with a ligating instrument secured thereto is sealed within an outer flexible package which maintains the instrument in the sterile condition. To remove the instrument from the package, the top panel of the package is stripped away, and the instrument is separated from the exposed retainer card.

The foregoing package poses several disadvantages for the packaging of a loop-type ligating instrument of the type described. For one, there is the possibility that during transit and/or handling of the package, the instrument will shift about within the package even to the point where the loop element may become disengaged from the semicircular extension at the end of the retainer card. Such an occurrence is aesthetically undesirable and, more importantly, could result in distortion of the shape of the loop making it more difficult to use the instrument. Another disadvantage of the package lies in the tendency of the loop to assume a relatively sharply cornered triangular set after being held in tensioned engagement with the semicircular extension of the retainer card for any length of time. Such a set, deviating from the preferred circular shape of the ligating loop, makes deployment of the instrument in a surgical operation more difficult.

SUMMARY OF THE INVENTION

It is an object of the present invention to provide a package for an endoscopic ligating instrument of the type which possesses a rigid elongate body containing a ligature which terminates outside the body in a contractible flexible loop, such package overcoming the disadvantages associated with the known ligating instrument package previously described.

It is a specific object of the invention to provide a ligating instrument package which is formed at least in part from transparent plastic thus allowing visual inspection of the instrument from both sides.

It is another particular object of the invention to provide a ligating instrument package which is relatively rigid and resistant to flexural distortion.

In keeping with these and other objects of the invention, there is provided a package for an endoscopic ligating instrument possessing an elongated tubular body and a ligature contained therein which terminates outside one end of the tubular body in a contractible ligating loop, the package comprising:

a) a relatively rigid instrument holding member having a base;

b) a first channel in the base of the instrument holding member for receiving the elongated tubular body of the instrument;

c) a ligating loop retaining member projecting upwardly from the base of the instrument holding member for receiving the ligating loop of the instrument therearound when the elongated tubular body of the instrument is received within the first channel of the instrument holding member, the ligating loop retaining member being configured to maintain the approximate shape of the ligating loop in an open position; and, d) a cover member adapted to be mounted to and to enclose the instrument holding member.

Unlike the known ligating instrument package described above, the package of this invention precludes the possibility of the shifting about of the ligating instrument during shipping and/or handling of the package. Moreover, since the ligating loop retaining member of the package herein possesses a configuration which retains the approximate shape of the ligating loop in the open position, the loop cannot assume a different shape during storage that might render the instrument more difficult to use or less efficacious in use.

BRIEF DESCRIPTION OF THE DRAWINGS

In the accompanying figures in which like reference numerals indicate like elements throughout:

FIG. 5 is a plan view of the instrument holding member of the package with the instrument removed therefrom;

FIG. 6 is a side elevational view of the instrument holding member of the package taken along line 6—6 of FIG. 5; and, FIGS. 7 and 8 are cross-sectional views of the instrument holding member of the package taken along lines 7—7 and 8—8, respectively, of FIG. 5.

DESCRIPTION OF THE PREFERRED EMBODIMENTS

Figure 1:
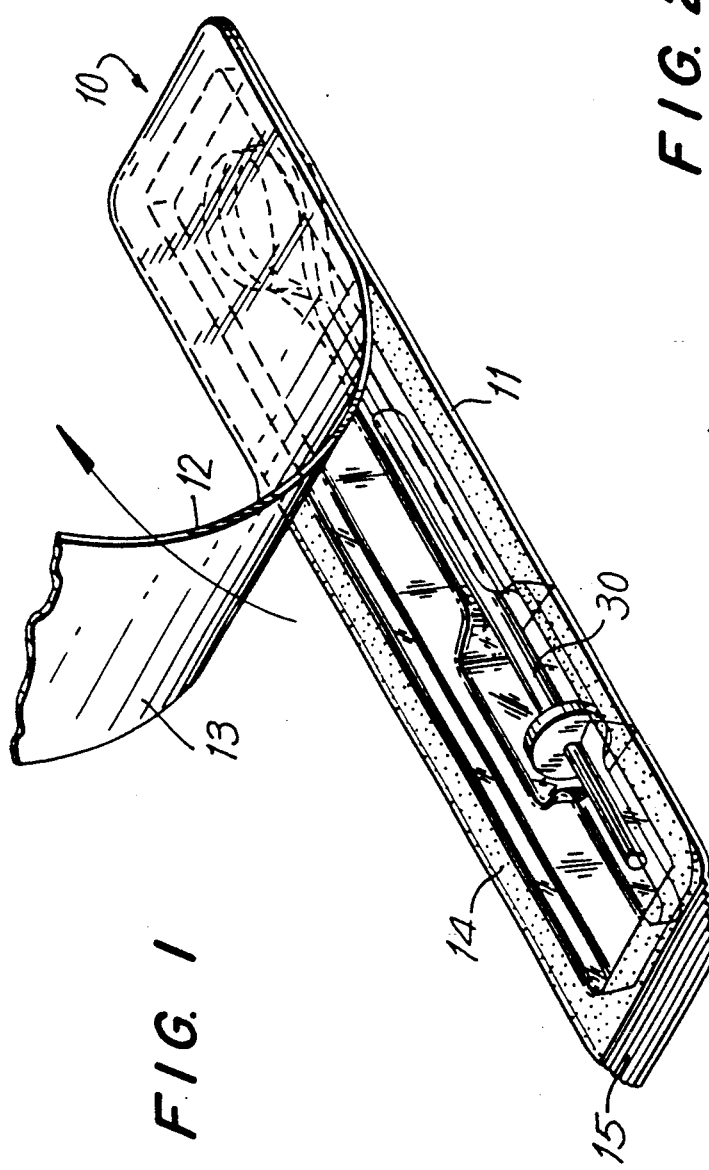
FIG. 1 is a perspective view of a ligating instrument package in accordance with the present invention with the cover member shown partially separated from the instrument holding member.
Figure 2:
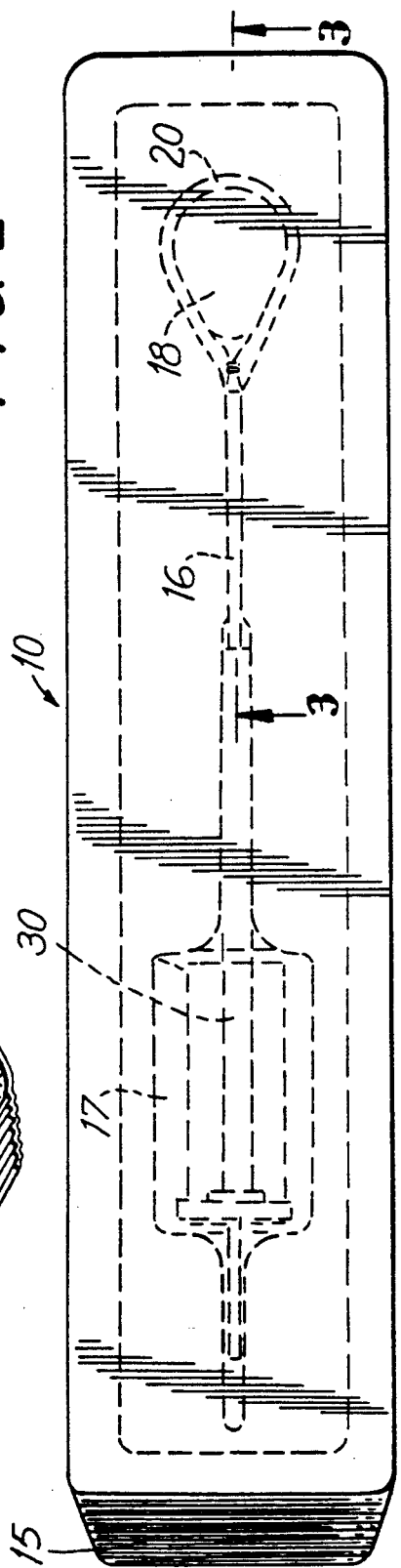
FIG. 2 is a plan view of the fully sealed ligating instrument package of FIG. 1.

As shown in FIGS. 1 and 2, endoscopic ligating loop package 10 holding a single ligating instrument 30, e.g., of the type disclosed in U.S. Pat. Nos. 3,476,114 and 3,476,115, the contents of which are incorporated by reference herein, includes a relatively rigid molded instrument holding member 11 and a peelable or strippable cover member 12 which is capable of maintaining the sterile condition of the package contents. Instrument holding member 11 and cover member 12 can be fabricated from any suitable materials. Advantageously, instrument holding member 11 is molded from a resin, and preferably a transparent resin, such as polyethylene terephthalate. Cover member 12 is advantageously formed from a spunbonded material, e.g., of high density polyethylene fibers such as Tyvek (Du Pont) which is ideal for ethylene oxide sterilization. Numerous other materials, both polymeric, non-polymeric and combinations thereof, e.g., aluminum foil-polymer laminates, can be utilized for the construction of instrument holding member 11 and/or cover member 12 as will be readily appreciated by those skilled in the art. In the sealed condition of the package, cover member 12 is bonded along its perimeter region 13 to perimeter region 14 of instrument holding member 11 employing any suitable adhesive. Knurled section 15 at the rearward end of instrument holding member 11 facilitates gripping of this member with one hand and pulling back cover member 12 with the other.

Figure 3:
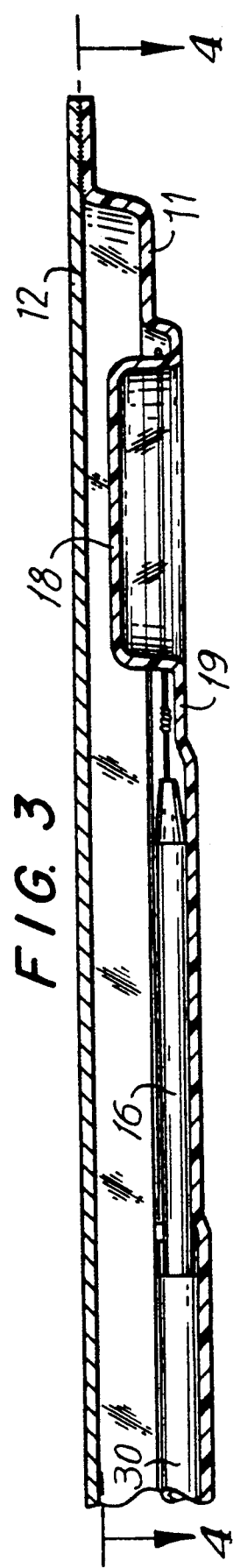
FIG. 3 is a side elevational view of the forward section of the ligating instrument package taken along line 3—3 of FIG. 2.
Figure 4:
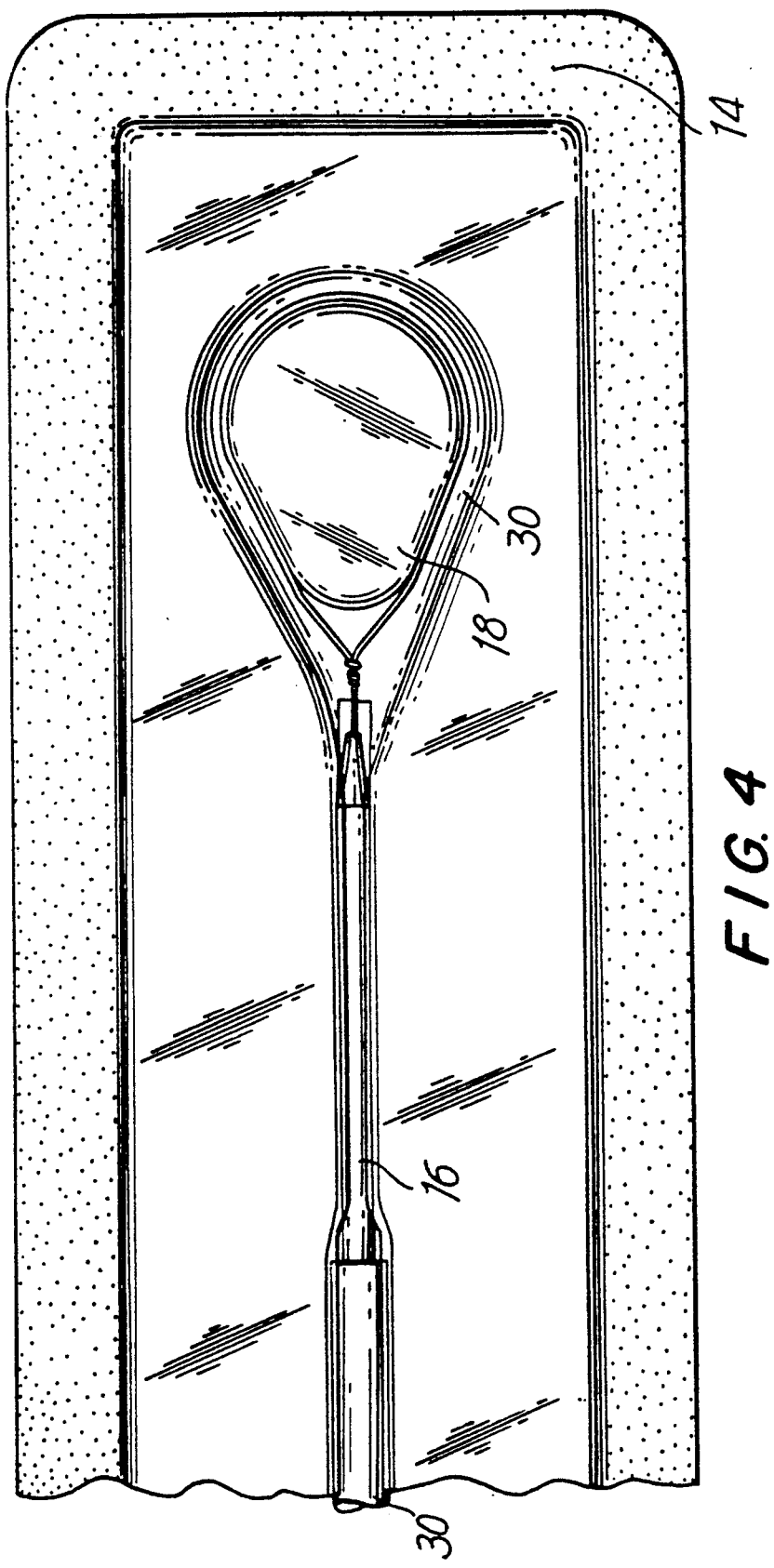
FIG. 4 is a plan view of the forward section of the ligating instrument taken along line 4—4 of FIG. 3.

As shown in FIGS. 2-4, the elongated tubular body of ligating instrument 30 occupies a first channel 16 which extends for at least the full length of the body and prevents the instrument from shifting about in the package, preferably through frictional engagement with the elongated tubular body. A well 17 is provided to facilitate the gripping and removal of instrument 30 from instrument holding member 11. At the forward section of instrument holding member 11, a ligating loop retaining member 18 which projects upwardly from base 19 of the holding member receives the ligating loop of instrument 30 and is configured in such a way, e.g., largely as a circle, so as to maintain the approximate shape of the loop in the open position. The height of loop retaining member 18 will ordinarily be sufficient to prevent disengagement of the ligating loop therefrom but not so high as to interfere with the mounting of cover member 12 upon holding member 11. Thus, when instrument 30 is removed from package 10, the loop will retain its generally circular shape which is the most advantageous for deployment of the instrument. A second channel 20 which communicates with first channel 16 can be provided so as to maintain the ligating loop in the same plane throughout the instrument.

Having now described the invention in specific detail and exemplified the manner in which it may be carried into practice, it will be readily apparent to those skilled in the art that innumerable variations, applications, modifications, and extensions of the basic principles involved may be made without departing from its spirit or scope.

What is claimed is:

1. A package for an endoscopic ligating instrument possessing an elongated tubular body and a ligature contained therein which terminates outside one end of the tubular body in a contractible ligating loop, the package comprising:
    a) a relatively rigid instrument holding member having a base;
    b) a first channel in the base of the instrument holding member for receiving the elongated tubular body of the instrument;
    c) a ligating loop retaining member possessing a maximum transverse dimension which is greater than the maximum transverse dimension of the first channel projecting upwardly from the base of the instrument holding member and positioned at one end of the first channel, the ligating loop retaining member receiving the ligating loop of the instrument therearound when the elongated tubular body of the instrument is received within the first channel of the instrument holding member, the ligating loop retaining member being configured to maintain the approximate shape of the ligating loop in an open position; and,
    d) a cover member adapted to be mounted to and to enclose the instrument holding member.

2. The package of claim 1 wherein the instrument holding member and/or the cover member are fabricated from a plastic.

3. The package of claim 1 wherein the instrument holding member is fabricated from a transparent plastic.

4. The package of claim 1 wherein the instrument holding member is fabricated form polyethylene terephthalate.

5. The package of claim 1 wherein the cover member is fabricated from spunbonded high density polyethylene fibers.

6. The package of claim 1 wherein the cover member is adhesively bonded to the instrument holding member such that the cover member can be peeled away from the instrument holding member.

7. The package of claim 1 wherein the ligating loop retaining member possesses an at least partially circular configuration.

8. The package of claim 1 wherein the ligating loop retainer is surrounded by a second channel which communicates with the first channel so as to maintain the ligating loop in substantially the same plane as the elongated body of the instrument.

9. The package of claim 1 further comprising a well defined in the instrument holding member, the well facilitating the gripping of the instrument and its removal from the instrument holding member.

10. The package of claim 1 wherein the first channel is adapted to frictionally engage the elongated tubular body of the instrument.

11. A sealed sterile package comprising:
    a) an endoscopic ligating instrument possessing an elongated tubular body and a ligature contained therein which terminates outside one end of the tubular body in a contractible ligating loop;
    b) a relatively rigid instrument holding member having a base receiving the instrument therein;
    c) a first channel in the base of the instrument holding member receiving the elongated tubular body of the instrument;
    d) a ligating loop retaining member projecting upwardly from the base of the instrument holding member and receiving the ligating loop of the instrument therearound, the ligating loop retaining member being configured to maintain the approximate shape of the ligating loop in an open position; and,
    e) a cover member enclosing the instrument holding member.

12. The package of claim 11 wherein the instrument holding member and/or the cover member are fabricated from a plastic.

13. The package of claim 11 wherein the instrument holding member is fabricated from a transparent plastic.

14. The package of claim 11 wherein the instrument holding member is fabricated form polyethylene terephthalate.

15. The package of claim 11 wherein the cover member is fabricated from spunbonded high density polyethylene fibers.

16. The package of claim 11 wherein the cover member is adhesively bonded to the instrument holding member such that the cover member can be peeled away from the instrument holding member.

17. The package of claim 11, wherein the ligating loop retaining member possesses an at least partially circular configuration.

18. The package of claim 11, wherein the ligating loop retainer is surrounded by a second channel which communicates with the first channel so as to maintain the ligating loop in substantially the same plane as the elongated body of the instrument.

19. The package of claim 11 further comprising a well defined in the instrument holding member, the well facilitating the gripping of the instrument and its removal from the instrument holding member.

20. The package of claim 11 wherein the first channel is adapted to frictionally engage the elongated tubular body of the instrument.

21. The package of claim 11 wherein the ligating loop retaining member is positioned at one end of the first channel and possesses a maximum transverse dimension which is greater than the maximum transverse dimension of the first channel.

* * * * *